(12) United States Patent
Ribnick et al.

(10) Patent No.: US 9,737,257 B2
(45) Date of Patent: Aug. 22, 2017

(54) ESTIMATING AND PREDICTING TOOTH WEAR USING INTRA-ORAL 3D SCANS

(71) Applicant: 3M INNOVATIVE PROPERTIES COMPANY, St. Paul, MN (US)

(72) Inventors: Evan J. Ribnick, St. Louis Park, MN (US); Guruprasad Somasundaram, Minneapolis, MN (US); Brian J. Stankiewicz, Mahtomedi, MN (US); Aya Eid, St. Paul, MN (US); Ravishankar Sivalingam, Woodbury, MN (US); Shannon D. Scott, Hudson, WI (US); Anthony J. Sabelli, Woodbury, MN (US); Robert D. Lorentz, North Oaks, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 260 days.

(21) Appl. No.: 14/609,529

(22) Filed: Jan. 30, 2015

(65) Prior Publication Data

US 2016/0220173 A1 Aug. 4, 2016

(51) Int. Cl.
*A61B 5/00* (2006.01)
*G06F 19/00* (2011.01)
*A61C 9/00* (2006.01)

(52) U.S. Cl.
CPC .......... *A61B 5/4557* (2013.01); *A61B 5/0062* (2013.01); *A61B 5/0088* (2013.01); *A61B 5/4547* (2013.01); *A61B 5/7275* (2013.01); *A61B 5/743* (2013.01); *G06F 19/30* (2013.01); *A61B 2576/02* (2013.01); *A61C 9/0053* (2013.01)

(58) Field of Classification Search
CPC ... A61B 5/4557; A61B 5/0062; A61B 5/0088; A61B 5/0013; A61B 5/4547; A61B 5/7275; A61B 5/743; A61B 6/14; A61B 6/5217; A61B 2576/02; A61C 9/0053; A61C 7/002; A61C 13/0004; A61C 19/05; G06F 19/30
See application file for complete search history.

(56) References Cited

U.S. PATENT DOCUMENTS

| | | | | |
|---|---|---|---|---|
| 6,099,314 A | * | 8/2000 | Kopelman | A61C 9/00 433/213 |
| 6,227,850 B1 | * | 5/2001 | Chishti | A61C 7/00 433/213 |

(Continued)

OTHER PUBLICATIONS

"3M True Definition Scanner" [on line], [retrieved from the internet on Sep. 11, 2014], URL <http://solutions.3m.com/wps/portal/3M/en_US/3M-ESPE-NA/dental-professionals/products/category/digital-materials/true-definition-scanner/>, pp. 1-2.

(Continued)

*Primary Examiner* — Manav Seth

(57) ABSTRACT

Methods for estimating and predicting tooth wear based upon a single 3D digital model of teeth. The 3D digital model is segmented to identify individual teeth within the model. A digital model of a tooth is selected from the segmented model, and its original shape is predicted. The digital model is compared with the predicted original shape to estimate wear areas. A mapping function based upon values relating to tooth wear can also be applied to the selected digital model to predict wear of the tooth.

16 Claims, 7 Drawing Sheets

(56) References Cited

U.S. PATENT DOCUMENTS

| | | | |
|---|---|---|---|
| 6,227,851 B1* | 5/2001 | Chishti | A61C 7/08 433/24 |
| 6,371,761 B1* | 4/2002 | Cheang | A61C 7/00 433/24 |
| 6,457,972 B1* | 10/2002 | Chishti | A61C 7/00 433/24 |
| 6,648,640 B2* | 11/2003 | Rubbert | A61C 7/00 433/24 |
| 6,766,217 B1 | 7/2004 | Hamada | |
| 7,077,647 B2* | 7/2006 | Choi | A61C 7/00 433/213 |
| 7,080,979 B2* | 7/2006 | Rubbert | G06F 19/3437 433/213 |
| 7,156,661 B2* | 1/2007 | Choi | A61C 7/002 433/213 |
| 7,442,041 B2* | 10/2008 | Imgrund | A61C 7/00 433/213 |
| 7,471,821 B2 | 12/2008 | Rubbert | |
| 7,605,817 B2 | 10/2009 | Zhang | |
| 7,695,278 B2 | 4/2010 | Sporbert | |
| 7,740,476 B2* | 6/2010 | Rubbert | G06F 19/3437 433/24 |
| 7,826,646 B2 | 11/2010 | Pavlovskaia | |
| 7,956,862 B2 | 6/2011 | Zhang | |
| 8,075,306 B2 | 12/2011 | Kitching | |
| 8,244,028 B2 | 8/2012 | Kuo | |
| 8,275,180 B2 | 9/2012 | Kuo | |
| 8,422,751 B2 | 4/2013 | Kim et al. | |
| 8,974,229 B2* | 3/2015 | Fisker | A61C 13/0004 433/220 |
| 9,526,599 B2* | 12/2016 | Kadobayashi | A61C 11/00 |
| 2005/0095562 A1 | 5/2005 | Sporbert et al. | |
| 2007/0024611 A1 | 2/2007 | Ingram | |
| 2008/0294405 A1* | 11/2008 | Kitching | A61C 7/08 703/11 |
| 2013/0054190 A1 | 2/2013 | Kadobayashi et al. | |
| 2016/0004811 A1* | 1/2016 | Somasundaram | G06F 17/50 703/11 |
| 2016/0070821 A1* | 3/2016 | Somasundaram | G06F 17/50 703/1 |
| 2016/0135925 A1* | 5/2016 | Mason | A61C 7/002 703/2 |

OTHER PUBLICATIONS

"Bruxism," Wikipedia, the free encyclopedia, [on line], [retrieved from internet on Sep. 15, 2014], URL:<http://en.wikipedia.org/wiki/Bruxism>, pp. 1.

Bardsley, "The evolution of tooth wear indices," Clinical Oral Investigations, 2008, vol. 12, No. 1, pp. S15-S19.

Belongie, "Shape Matching and Object Recognition Using Shape Contexts." IEEE Transaction Pattern Analysis and Machine Intelligence, Apr. 2002, vol. 24, No. 24, pp. 509-522.

Cortes, "Support-Vector Networks," Machine Learning, 1995, vol. 20, pp. 273-297.

Hilaga, "Topology Matching for Fully Automatic Similarity Estimation of 3D Shapes," Proceedings of the 28th Annual Conference on Computer Graphics and Interactive Techniques, 2001, pp. 203-212.

Johnson, "Using Spin Images for Efficient Object Recognition in Cluttered 3D Scenes," IEEE Transaction on Pattern Analysis and Machine Intelligence, 1999, vol. 21, No. 5, pp. 433-449.

Kalogerakis, "Learning 3D mesh segmentation and Labelling," ACM Transactions on Graphics, 2010, vol. 102, pp. 1-13.

Kondo, "Tooth Segmentation of Dental Study Models Using Range Images," IEEE Transactions on Medical Imaging, Mar. 2004, vol. 23, No. 3, pp. 350-362.

Koyano, "Assessment of bruxism in the clinic," Journal of Oral Rehabilitation, Jul. 2008, vol. 35, pp. 495-508.

Kumar, "Improved Segmentation of Teeth in Dental Models," Computer-Aided Design and Applications, 2011, vol. 8, No. 2, pp. 211-224.

Lafferty, "Conditional Random Fields: Probabilistic Models for Segmenting and Labeling Sequence Data," Proceedings of the Eighteenth International Conference on Machine Learning, 2001, pp. 282-289.

Lazebnik, "Beyond Bags of Features: Spatial Pyramid Matching for Recognizing Natural Scene Categories," IEEE Conference on Computer Vision and Pattern Recognition, 2006, vol. 2, pp. 2169-2178.

Liu, "A Part-aware Surface Metric for Shape Analysis," Computer Graphics Forum, Blackwell Publishing Ltd, 2009, vol. 28, No. 2, pp. 397-406.

Marbach, "Reliability of clinician judgments of bruxism," Journal of Oral Rehabilitation, 2003, vol. 30, pp. 113-118.

Quinlan, "Induction of Decision Trees," Machine Learning 1, 1986, pp. 81-106.

Rusinkiewicz, "Efficient Variants of the ICP Algorithm," IEEE Third International Conference on 3-D Digital Imaging and Modeling, 2001, pp. 1-8.

Shapira, "Consistent mesh partitioning and skeletonisation using the shape diameter function," The Visual Computer, Jan. 2008, vol. 24, pp. 249-259.

PCT International Search Report for PCT/US2016/013329, mailed May 2, 2016.

\* cited by examiner

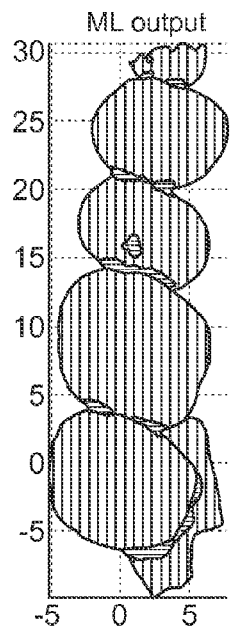 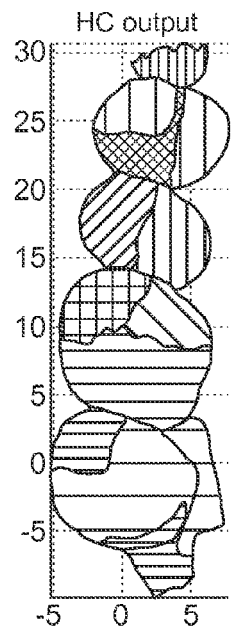 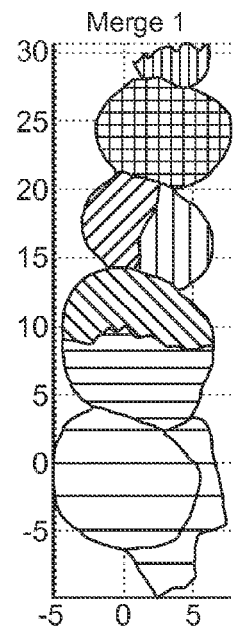 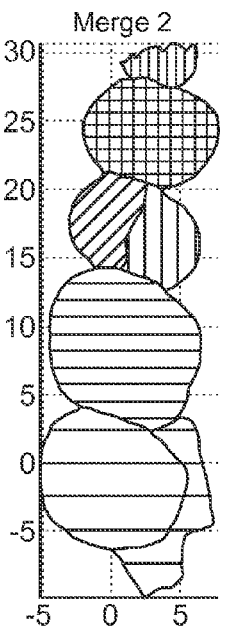
*Fig. 9A*   *Fig. 9B*   *Fig. 9C*   *Fig. 9D*
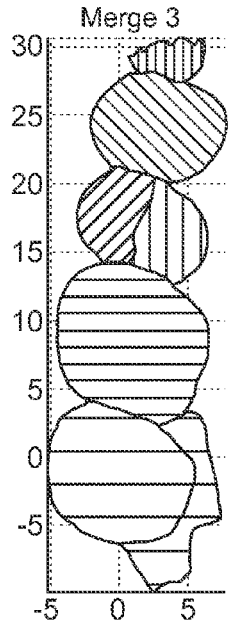 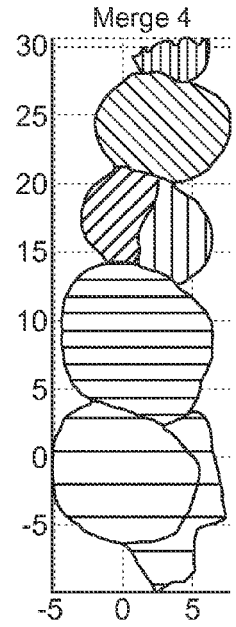 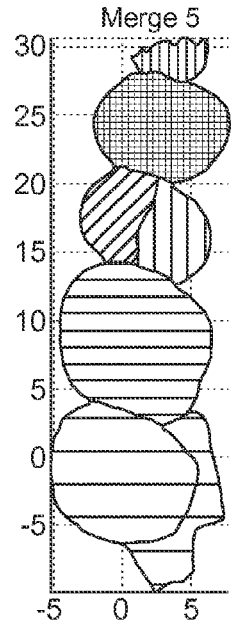 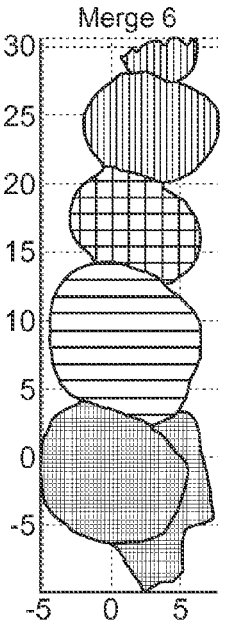
*Fig. 9E*   *Fig. 9F*   *Fig. 9G*   *Fig. 9H*

ESTIMATING AND PREDICTING TOOTH WEAR USING INTRA-ORAL 3D SCANS

BACKGROUND

Tooth wear (associated with Bruxism) and gingival recession are both conditions that, if not treated in a timely manner by dental professionals, can have serious medical consequences. In the case of Bruxism, lateral movements and tooth grinding can cause significant tooth wear and lead to muscle pain, temporomandibular joint issues, and headaches. In some cases, this may lead to the dentin being exposed, dental decay, and even tooth fracture. Despite the potential severity of these consequences, the tools available to dental professionals for diagnosing and assessing the severity of tooth wear and gingival recession are limited. In the case of tooth wear, these tools include patient questionnaires, clinical examination by a dentist, and bite force measurements. Clinical examinations may be performed using the Individual Tooth-Wear Index, which provides a rating between 0 and 3 based on visual assessment by a dentist. Accordingly, a need exists for additional tools to assess tooth wear, particularly using intra-oral 3D scans.

SUMMARY

A first method for estimating teeth wear, consistent with the present invention, includes receiving a 3D digital model of teeth and segmenting the 3D digital model of teeth to identify individual teeth within the 3D digital model of teeth. A digital model of a tooth is selected from the segmented 3D digital model of teeth, and an original shape of the selected tooth is predicted to obtain a digital model of a predicted original shape. The digital model of the tooth is compared with the digital model of the predicted original shape to estimate wear areas in the tooth.

A second method for predicting teeth wear, consistent with present invention, includes receiving a 3D digital model of teeth. A mapping function is applied to the digital model of the teeth based upon values relating to tooth wear. Wear areas in the teeth are predicted based upon the applying step.

BRIEF DESCRIPTION OF THE DRAWINGS

The accompanying drawings are incorporated in and constitute a part of this specification and, together with the description, explain the advantages and principles of the invention. In the drawings.

FIGS. 9A-9H illustrate merging of the results of segmentation methods to segment teeth in a 3D digital model;

DETAILED DESCRIPTION

Embodiments includes analyzing tooth wear from a single 3D scan of the patient's dentition. One approach is based on estimating the original shape of the surface through use of a database (or collection) of known tooth shapes and learned mathematical model and for reconstructing shape, and then comparing this estimated original shape with the current shape of the surface. Another approach is based upon comparing the current shape of the surface with annotated scans where the annotation indicates an amount of tooth wear.

A method for determining tooth wear based upon comparison of multiple 3D scans of a patient is described in U.S. patent application Ser. No. 14/321,318, entitled "Detecting Tooth Wear Using Intra-Oral 3D Scans," and filed Jul. 1, 2014, which is incorporated herein by reference as if fully set forth.

3D Scan Acquisition and Segmentation

Figure 1:
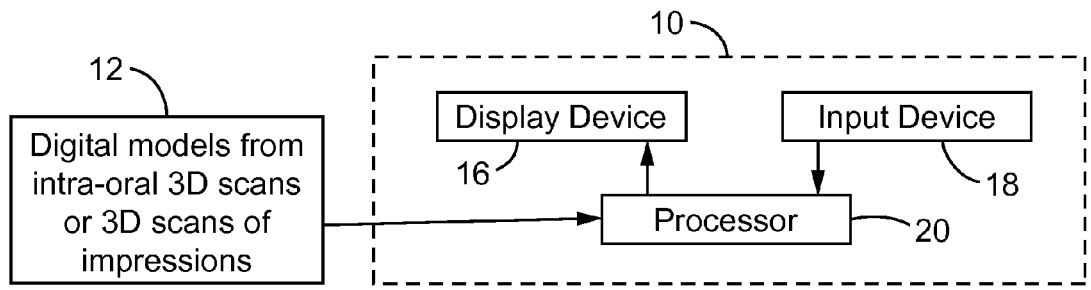
FIG. 1 is a diagram of a system for detecting tooth wear using a 3D digital model based upon intra-oral 3D scans.
Figure 2:
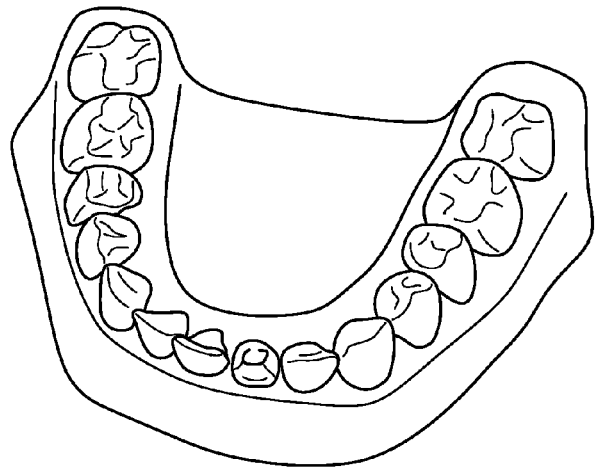
FIG. 2 illustrates a 3D model of teeth from intra-oral scans.

FIG. 1 is a diagram of a system 10 for detecting tooth wear using a digital 3D model based upon intra-oral 3D scans. System 10 includes a processor 20 receiving digital 3D models of teeth (12) from intra-oral 3D scans or scans of impressions of teeth. System 10 can also include an electronic display device 16, such as a liquid crystal display (LCD) device, for displaying indications of tooth wear and an input device 18 for receiving user commands or other information. An example of digital 3D model of a patient's teeth from a scan is shown in FIG. 2. Systems to generate digital 3D images or models based upon image sets from multiple views are disclosed in U.S. Pat. Nos. 7,956,862 and 7,605,817, both of which are incorporated herein by reference as if fully set forth. These systems can use an intra-oral scanner to obtain digital images from multiple views of teeth or other intra-oral structures, and those digital images are processed to generate a digital 3D model representing the scanned teeth. System 10 can be implemented with, for example, a desktop, notebook, or tablet computer. System 10 can receive the 3D scans locally or remotely via a network.

Figure 3:
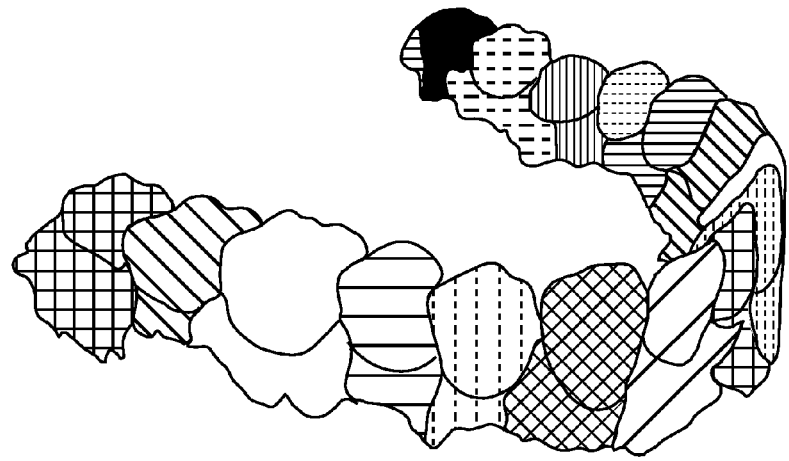
FIG. 3 illustrates a 3D model of teeth segmented to digitally separate each tooth.

For certain diagnostic tasks, the individual teeth in the model need to be segmented from one another before the desired analysis or manipulation can be performed. In some cases, a software interface may be presented in order for a user to perform this segmentation, or some parts of it, manually. However, this process can be quite labor intensive and tedious. As such, the automation of this task is desirable. An example of teeth that have been segmented in a digital model is shown in FIG. 3. The segmentation provides for separating individual teeth in the digital 3D model, as represented by the shading in FIG. 3, and each tooth in the model can essentially be digitally separated from the other teeth for further processing to detect tooth wear. Using a segmented digital 3D model for comparing or analyzing individual teeth is more accurate than comparing whole or partial arches within the model.

Described herein are techniques for tooth segmentation within a digital 3D model. The technique is a combination of two separate algorithms and combines the strengths of both of them. The first algorithm is a geometric hill-climbing approach which takes into account topological structures such as height and curvature. The second algorithm is a machine learning approach which classifies each point on the surface as belonging to either a boundary or a non-boundary. Alternatively, the second algorithm is interstice detection which classifies a set of planes (or points) that approximate the intersticial spaces between teeth. The second algorithm can be complementary to the first algorithm (geometric hill-climbing) and combined with the first algorithm to produce a resulting segmentation. As another alternative to the second algorithm, the first algorithm can be combined with user input estimating centroids of teeth in the digital 3D model. Instead of merging the results of two algorithms, only one algorithm can be used to segment the digital 3D model such as any one of the algorithms described herein.

The 3D scans addressed herein are represented as triangular meshes. The triangular mesh is common representation of 3D surfaces and has two components. The first component, referred to as the vertices of the mesh, are simply the coordinates of the 3D points that have been reconstructed on the surface—i.e., a point cloud. The second component, the mesh faces, encodes the connections between points on the object and is an efficient way of interpolating between the discrete sample points on the continuous surface. Each face is a triangle defined by three vertices, resulting in a surface that can be represented as a set of small triangular planar patches.

Figure 4:
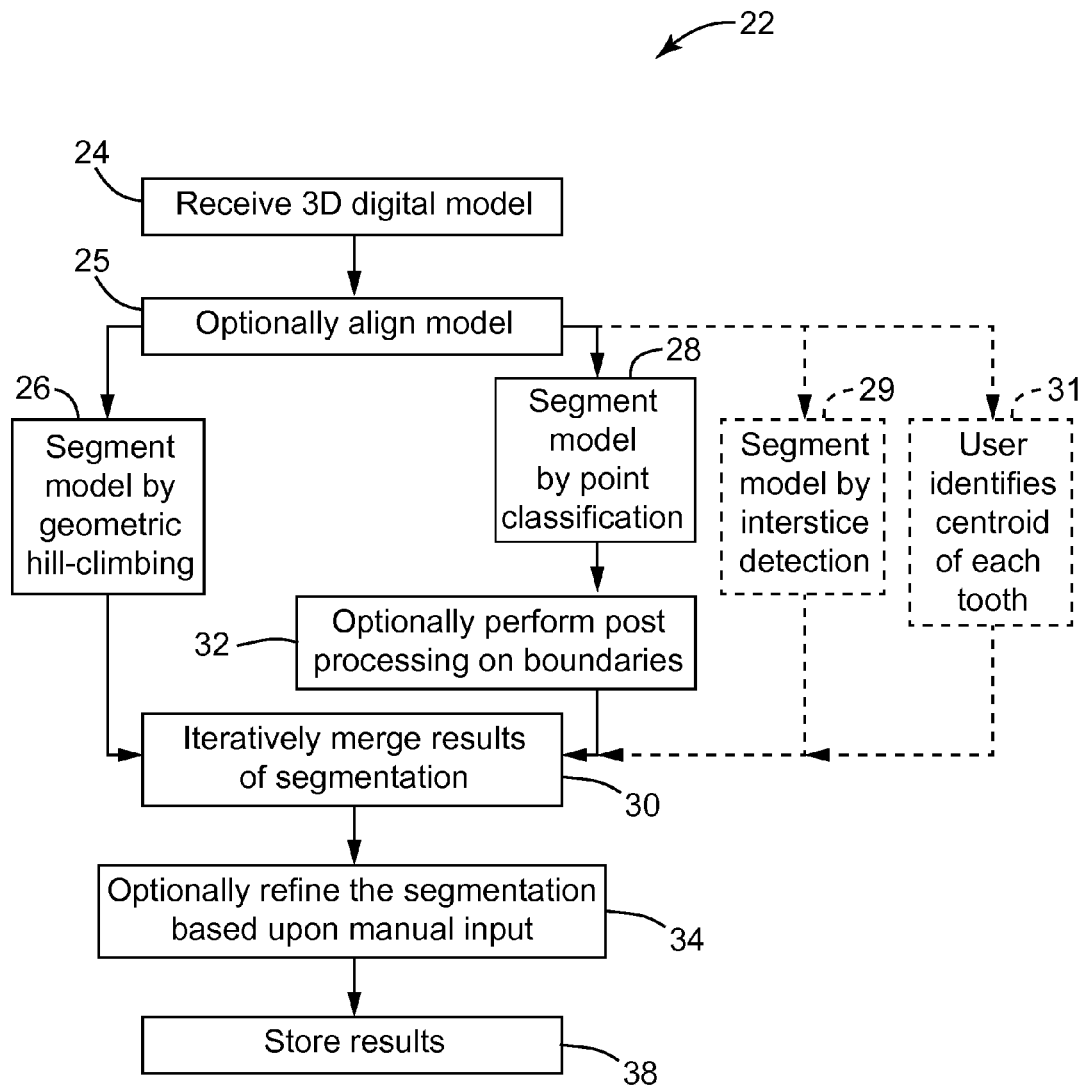
FIG. 4 is a flow chart of a method for segmenting teeth in a 3D digital model.

FIG. 4 is a flow chart of a method 22 for segmenting teeth in a digital 3D model. Method 22 can be implemented in software or firmware modules, for example, for execution by processor 20. Method 22 can alternatively be implemented in hardware modules or a combination of software and hardware.

Method 22 includes receiving a digital 3D model of a patient's teeth (step 24) and optionally aligning the model (step 25). Method 22 then involving segmenting the model by geometric hill-climbing (step 26) and point classification (step 28). Optionally, post processing on boundaries of the segmentation by point classification is performed (step 32). As an alternative to point classification, the model can be segmented by interstice detection (step 29). As another alternative to point classification, method 22 can receive user input identifying centroids of each tooth in the model (step 31).

The results of the segmentation methods are iteratively merged (step 30). In particular, the results of segmentation by hill-climbing are merged with the results of segmentation by point classification or interstice detection or user input identifying the centroids. The merged segmentation can optionally be refined based upon manual, for example user-entered, input (step 34). The results of the segmentation are stored (step 38). The segmentation results in a separate mesh for each tooth from the digital 3D model, as illustrated in FIG. 3. These steps are described in more detail below.

The optional alignment step 25 can be implemented using a Support Vector Regression (SVR) method to find the occlusal plane fitted to a mesh of the teeth in the digital 3D model. The alignment can be used to have the teeth in the digital 3D model essentially aligned with the Y axis.

The alignment can use the LIBSVM toolbox and $\epsilon = SVR$ method. The kernel is chosen to be linear and $\epsilon=5$. The training is based on the assumption that teeth are roughly pointing up along the Y axis. The output is sample points from the occlusal plane which is given to a simple principal component analysis (PCA) method to find the normal direction. SVR uses a linear loss function with a zero part within the margins which performs better for teeth dataset than the quadratic loss function in regular least square regression methods. It helps to decrease the effect of gingiva cut-lines which can be very jagged and bumpy in mesh scans. It also tries to rule out the vertical points on the teeth (buccal part) and give more weight of importance to the horizontal points on teeth (cuspal part) in determining the occusal plane orientation. The RANSAC method and Robust PCA method can alternatively be used for the alignment.

Table 1 provides exemplary pseudocode for implementing the alignment step.

TABLE 1

Pseudocode for Normal Direction Extraction

Input: a 3D mesh with a set of vertices V specified in 3D coordinate system X, Y and Z. Y represents the rough direction of vertical axis in which the teeth point upwards.
Output: the normal vector perpendicular to occlusal plane which represents the correct upward direction of teeth.
Assumptions: Teeth are roughly pointing up along the Y axis. The mesh has been truncated below the gum line.
Method steps:
1  Subtract the mean of data points to centralize the data points around (0,0,0).
2  Apply the Support Vector Regression with linear kernel and margin value $\epsilon$ to find the occlusal plane.
3  Find the normal direction of the occlusal plane by geometrical methods or applying a simple PCA.

Segmentation by Geometric Hill-Climbing

One of the algorithms for segmentation is based upon geometric operations on the mesh. Specifically, the main idea behind this approach is that, if one starts from any point on the surface and moves upwards through a series of points, one will converge to a high point that is a local maximum. In most cases it would be expected all points on a tooth (or on the same cusp of a tooth) will converge to the same local maximum. This type of segmentation can produce very accurate boundaries between teeth, but it typically results in an over-segmentation in which a single tooth may be divided into multiple segments.

Before performing the segmentation, the mesh is preprocessed using Laplacian smoothing. This preprocessing is an effective way of removing high-frequency noise in the surface reconstruction.

An energy function is then computed for each vertex on the mesh, on which the algorithm will attempt to find local maxima later in the hill-climbing process. The energy function at each vertex is composed of two terms, where for the i-th vertex:

$$f_i = y_i + \lambda d_i$$

where $y_i$ is the y-coordinate (height) of the i-th vertex, $d_i$ is its angular divergence, and $\lambda > 0$ is a weighting parameter. The parameter $\lambda$ can be any value greater than zero or, alternatively, $\lambda$ can be equal to zero.

Angular divergence is a measure of overall curvature around a point. For a face F comprised of vertices $v_i$, $v_j$, and $v_k$, with normal vectors $n_i$, $n_j$, and $n_k$, respectively, the angular divergence is given by:

$$D_f = |\cos^{-1}(n_i^T n_j)| + |\cos^{-1}(n_j^T n_k)| + |\cos^{-1}(j_n^T n_k)|$$

If the area around a face is completely flat, then all the normal vectors of all three of its vertices will point in the same direction, and the DE will be zero. Then the angular divergence of the i-th vertex $v_i$ is the mean of the angular divergences of the faces of which $v_i$ is a part.

Once the energy $f_i$ is computed for each vertex, segmentation is performed according to a hill-climbing procedure. Conceptually, the algorithm can be understood as follows. For each vertex on the surface, the algorithm initializes a hill-climb, in which at each iteration it moves to the connected neighbor (as defined by the faces) that has the highest energy function value. The algorithm continues climbing until it reaches a local maximum that has higher energy than all of its neighbors. All vertices that were passed through along this route are assigned to this local maximum, and all such paths that converge to this local maximum define a segment. This process is repeated until all vertices on the mesh have been traversed.

This segmentation assigns vertices to segments defined by local energy maxima that can be reached through a monotonically-increasing path through the energy function. The energy function $f_i$ is defined such that each iteration of hill-climbing moves upwards in height, but is discouraged from crossing an area with high curvature by the angular divergence term. This helps ensure that the boundaries between teeth are not crossed.

Figure 5:
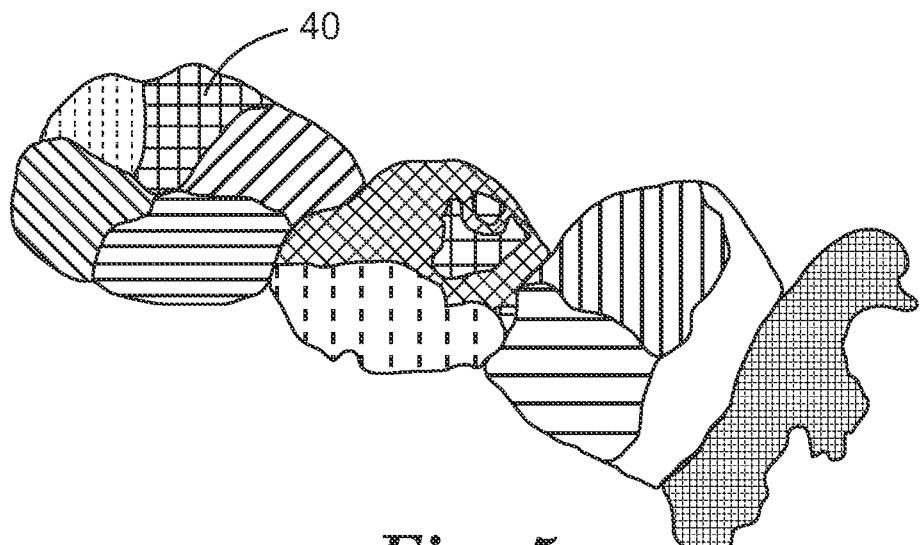
FIG. 5 illustrates over-segmentation of teeth by a geometric hill-climbing method.

An example of a segmentation produced by this algorithm is shown in FIG. 5. As can be seen, the algorithm over-segments the teeth by separating each cusp of a tooth into its own segment—this can be understood intuitively as a result of the hill-climbing procedure, since each cusp will have its own unique local maximum. For example, the digital model of tooth 40 is segmented into five sections. However, the boundaries produced by this approach are quite precise and accurately separate teeth from one another.

Table 2 provides exemplary pseudocode for implementing the geometric hill-climbing algorithm.

TABLE 2

Pseudocode for Hill-Climbing Segmentation

Input: a 3D mesh with a set of vertices V specified in 3D coordinate system X, Y and Z. Y represents the vertical axis or the general direction in which the teeth point upwards. The mesh also has a set of triangulations or faces F based on the vertices.
Output: Segmented mesh, where for each vertex $v_i$ in the mesh, a label $l_i$ corresponding to the segment to which that vertex belongs is assigned.
Assumptions: Teeth are roughly pointing up along the Y axis. The mesh has been truncated below the gum line.
Method steps:
1  Perform mesh Laplacian smoothing to reduce error
2  For each vertex $v_i$ in V, compute the surface normal at that vertex
3  For each face $f_i$ in F, compute the divergence of the face as $D_f = |\cos^{-1}(n_i^T n_j)| + |\cos^{-1}(n_j^T n_k)| + |\cos^{-1}(j_n^T n_k)|$ where $n_i$, $n_j$ and $n_k$ are the normal directions of vertices i, j, and k of the face
4  Apply the divergence value of every face to all the individual vertices of the face
5  Compute the energy function value at each vertex as y + lambda * $D_f$
6  For each vertex determine the maximum function value in a local neighborhood
7  Assign all vertices to a segment assigned to the local maximum value in step 6
8  Repeat steps 6 to 7 until a local maximum is reached
9  Assign the appropriate cluster labels to each vertex Segmentation by Point Classification The segmentation by point classification is a data-driven approach. Unlike the geometric hill-climbing approach, this approach relies on manually provided groundtruth segmentation. Groundtruth can be obtained from a user providing nearly accurate segmentation manually using mesh manipulation tools such as the MeshLab system. A selection of an individual tooth can be made using a face selection tool. Individual teeth are selected in this manner and saved as individual mesh files. Using the original mesh and the individual teeth files, a labeling of the vertices in the original mesh can then be inferred. Once groundtruth for a full scan is completed, the inferred labels of all the segments can be visualized.

From this groundtruth labeling, the boundary vertices between segments can be determined. For each vertex the distribution of vertex labels around that vertex is examined. If the distribution is not unimodal (i.e., the vertex labels are predominantly the same), then that vertex is considered an interior vertex. If not, the vertex is considered a boundary vertex. This data can be manually entered one time, for example, as training data and then used repeatedly in the point classification algorithm.

Figure 6:
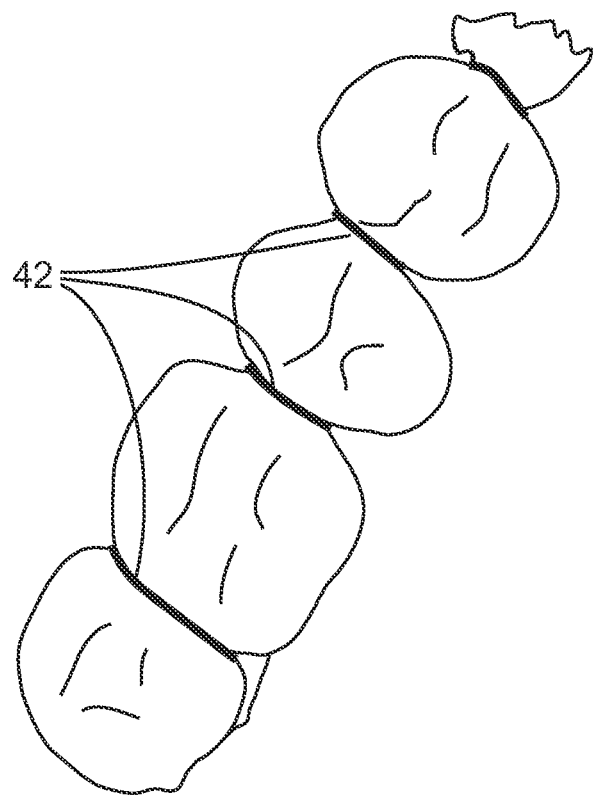
FIG. 6 illustrates detection of boundary vertices between teeth in a 3D digital model.

Given the groundtruth boundary vertices labels from multiple training meshes, the algorithm provides for a function that is capable of predicting whether a vertex on a mesh lies in the interior of a tooth or on the boundary between teeth. In particular, the algorithm can classify or label points in the mesh as being on a tooth or on a boundary between teeth. This process involves two tasks: feature extraction and classification. FIG. 6 illustrates detection of boundary vertices 42 between teeth in a digital 3D model.

Table 3 provides exemplary pseudocode for implementing the point classification (machine learning) training data algorithm.

TABLE 3

Pseudocode for Machine Learning Training

Input: Multiple 3D meshes with a sets of vertices V specified in 3D coordinate system X, Y and Z. Y represents the vertical axis or the general direction in which the teeth point upwards. The mesh also has a set of triangulations or faces F based on the vertices. Also the groundtruth segmentation in the form of the vertices corresponding to boundaries and those in the interior as indicated by manual annotation.
Output: A predictive model that is capable of generating the boundary vertex prediction labels for a query set of vertices.
Assumptions: Teeth are roughly pointing up along the Y axis. The mesh has been truncated below the gum line.
Method steps:
1  For each vertex in every mesh in the training set of data, compute the following features:
   a. Normal direction
   b. Absolute, mean and Gaussian curvature
   c. Shape context
   d. Mesh fourier
   e. Spin image
   f. Mesh local covariance
2  Construct a data matrix X which is M X N where M is the total number of vertices in all the meshes and N is the total number of feature dimensions when all features in step 1 are concatenated
3  Train a RUSBoosted decision tree classifier that can predict the labels corresponding to whether a vertex lies on the boundary or not. (An alternate classifier can be used.)

Feature Extraction

In order to perform this task, the point classification algorithm extracts many characteristic features for every vertex in the mesh. It is often difficult to determine which features are useful in a segmentation algorithm. There are many features which can be used for segmentation in this framework, including but not limited to multi-scale surface curvature, singular values extracted from PCA of local shape, shape diameter, distances from medial surface points, average geodesic distances, shape contexts, and spin images. Of these, the algorithm implements the following features: absolute and mean curvature, direction of normal at vertex, local covariance of the mesh around the vertex and its principal Eigen values, spin images, Fourier features, shape contexts, and PCA features.

Classification

Given the feature set for a vertex X, the function f is defined as follows: f: X→{1,0}, that is the function f maps the set of features X to either a 1 or 0. A value 1 indicates that vertex is a boundary vertex and the value 0 indicates otherwise. This function can be one or a combination of many classification methods such as support vector machines, decision trees, conditional random fields, and the like. Additionally, in the segmentation as a classification problem, there is a class imbalance. The number of interior vertices is much greater than the number of boundary vertices. The ratio of interior vertices to boundary vertices is typically 100:1. In such extreme class imbalance situations, regular classifiers are not optimal. This is because it is possible to obtain very high accuracy by always predicting that a vertex is in the interior, and that would be practically useless since no vertices would be classified as being on a boundary. To remedy this issue, one option involves using classifier ensembles such as boosting.

The classification algorithm uses RUSBoosting on decision stumps as a classifier. RUSBoost stands for random undersampling boosting and is known to handle the class imbalance very well. Additionally RUSBoost is already implemented in the MATLAB program "fitensemble" function. Based on preliminary analysis, RUSBoost was performed on 700 decision stumps. This number was chosen using cross-validation on the training set with the resubstitution loss as the metric. For our experiments, we used a "leave-scan-out" cross-validation scheme. Our dataset consisted of 39 scans, and for every test scan the remaining 38 scans were used for training. The resulting predictions were compared to the groundtruth boundary labels of the test scan. A confusion matrix can then be obtained by comparing the groundtruth labels with the predicted labels. From this we obtained the false alarm rate and the hit rate. With cross-validation testing on 39 scans we obtained an 80% hit rate and 1.7% false alarm rate on average.

Table 4 provides exemplary pseudocode for implementing the point classification (machine learning) algorithm.

TABLE 4

Pseudocode for Machine Learning Prediction

Input: a 3D mesh with a set of vertices V specified in 3D coordinate system X, Y and Z. Y represents the vertical axis or the general direction in which the teeth point upwards. The mesh also has a set of triangulations or faces F based on the vertices.
Output: Binarized mesh where for each vertex $v_i$ in the mesh, a label $l_i$ corresponding to whether the vertex belongs to a boundary or not.
Assumptions: Teeth are roughly pointing up along the Y axis. The mesh has been truncated below the gum line.
Method steps:
1   For each vertex $v_i$ in V, compute the following features:
    a. Normal direction
    b. Absolute, mean and Gaussian curvature
    c. Shape context
    d. Mesh fourier
    e. Spin image
    f. Mesh local covariance
2   Construct a data matrix X which is M X N where M is the number of vertices in the mesh and N is the total number of feature dimensions when all features in step 1 are concatenated
3   Predict using the learned decision tree RUSBoost classifier the labels corresponding to whether a vertex lies on the boundary or not

Segmentation by Interstice Detection

As an alternative to point classification, the second algorithm for segmentation can use interstice detection (step 29 in method 22). Table 5 provides exemplary pseudocode for implementing the interstice detection algorithm.

TABLE 5

Pseudocode for Interstice Detection

Input: a 3D mesh with a set of vertices V specified in 3D coordinate system X, Y and Z. Y represents the vertical axis or the general direction in which the teeth point upwards. The mesh also has a set of triangulations or faces F based on the vertices.
Output: a set of planes that approximate the intersticial spaces between each pair of teeth.
Assumptions: Teeth are roughly pointing up along the Y axis.
Method steps:
1  Form a plan-view range image of the mesh. That is, a range image from the top view, where each pixel represents the height of the surface at the corresponding point.
2  Estimate a one-dimensional parameterization of the dental arch using the Locally-Linear Embedding (LLE) algorithm, which results in a curve that represents the general shape of the arch and passes roughly through the centers of the teeth.
3  Compute a set of evenly-spaced sample points along the one-dimensional parameterization.
4  For each sample point along the curve, compute the sum of heights in the range image along a line normal to the curve at that point.
5  Intersticial spaces are identified as sample points that are local minima in the sum of heights computed in step 4. The orientation of the intersticial space is given by the direction of the normal to the one-dimensional parameterization curve at the corresponding sample point.
6  Detected intersticial spaces, and their orientations, are mapped back to the three-dimensional coordinates of the original mesh.

Morphological Clean Up

Figure 7A:
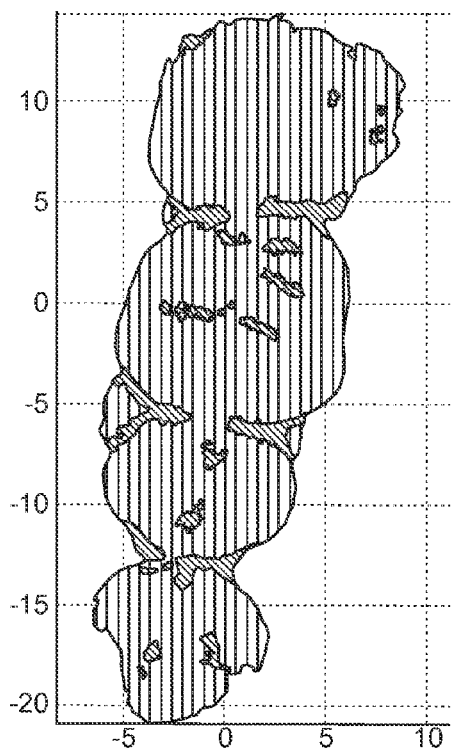
FIGS. 7A and 7B illustrate morphological clean up to fix boundaries between teeth in a 3D digital model.
Figure 7B:
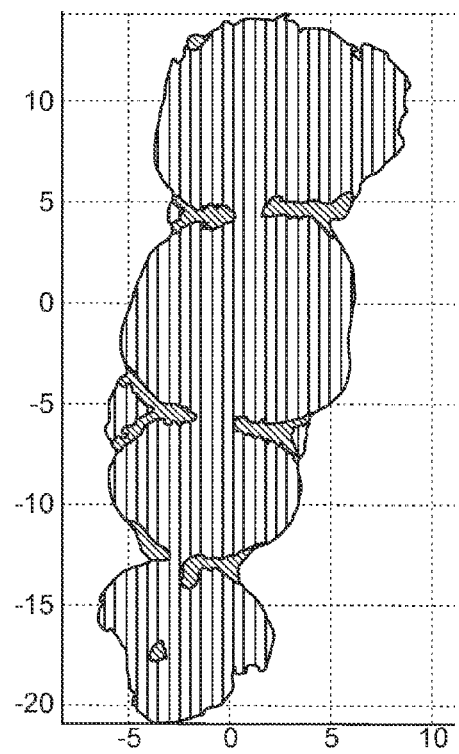

Morphological operations such as mesh erosion and dilation can be done in tandem, resulting in an operation known morphological opening. Unlike images, mesh erosion and dilation are non-trivial since there are no sliding windows. Instead to perform mesh erosion, one can use the connected v-ring of every vertex as its neighborhood. Performing morphological opening removes islands and small streaks which can interfere with the merging algorithm mentioned later. FIGS. 7A and 7B illustrate morphological clean up to fix boundaries between teeth in a digital 3D model with FIG. 7B illustrating clean up of the boundaries shown in FIG. 7A. This morphological clean up can be used to for the optional step 32 in method 22 after the segmentation by point classification.

Complementary Approaches to Segmentation

Based on the results of the hill-climbing approach and the classification approach, it was observed that the hill-climbing captures the general geometry of cusp and has a tendency to form good boundaries around teeth, but it over-segments and thus creates more false boundaries. The classification approach on the contrary has a somewhat less than desired hit rate on boundaries but has a very low false alarm rate. From this complementary result, a method to merge the results helps reduce the demerits of both approaches and boost the merits of both. In order to accomplish this, a hierarchical merging algorithm is used, which merges the segments in the hill-climbing approach using the boundary predictions of the classification approach. Every boundary predicted by the hill-climbing approach is given a score based on the predicted boundary vertices from the classification approach. Then a hierarchical merging is performed. All the boundaries with a score less than a threshold are discarded and the corresponding segments are merged and the boundary scores are corrected accordingly. This threshold is gradually increased. For example, all boundaries that have score less than 5 are discarded first. The corresponding segments are merged, and then this process is repeated by increasing the threshold step-by-step to, for example, 50. This heuristic provides correct segmentation of the teeth in one of the merge steps in most cases.

Elimination of Non-Aligned Boundaries

Figure 8A:
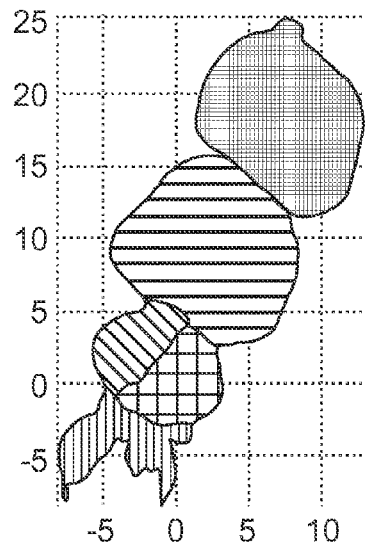
FIGS. 8A and 8B illustrate removal of non-aligned boundaries in 3D digital model.
Figure 8B:
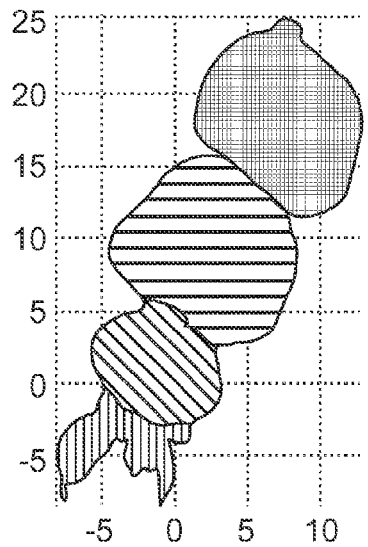

Even after the merging process, there are some strong false boundaries predicted by the machine learning classifier which are not eliminated completely. These boundaries can be removed using a hypothesis of boundary direction alignment. Since each consecutive tooth boundary is roughly parallel, there cannot be any stark changes in the boundary direction between consecutive teeth. In FIGS. 8A and 8B, a misaligned boundary is removed using such a hypothesis where FIG. 8B illustrates removal of a boundary from the model of FIG. 8A. This can be achieved by determining the principal direction of orientation of each boundary segment using PCA. The principal components (PCs) of each consecutive tooth boundary should be aligned, thus resulting in eliminating the boundaries which have misaligned PCs. This process is applied after merging the hill climbing result with the machine learning result.

Segmentation Results

Sample results of the classification or machine learning (ML), hill-climbing (HC), and the merging steps are shown in FIGS. 9A-9H. The machine learning output (FIG. 9A) shows the mesh labeling for the boundary vertices and the interior vertices. The second mesh (FIG. 9B) is the result of the hill climbing. As shown in FIG. 9B, the hill-climbing over-segments each tooth but in general there is a reduced chance of a segment being shared across teeth. This is also a behavior associated with the choice of the parameter $\lambda$. The meshes displayed in FIGS. 9C-9H indicate iteratively the result of each merge step. Merge 1 corresponds to discarding boundaries with a score less than 5 and merge 2 corresponds to scores less than 10 and so on. In this example, the correct segmentation was achieved at step 6. As shown in the example of FIGS. 9C-9H, it is possible there are no changes between some of the successive (iterative) merge steps. Successive merge steps indicate how aggressively nearby segments are merged and, therefore, in some cases changes are only noticeable at later merge steps.

The score used for merging can represent, for example, the number of points classified as a boundary from the point classification algorithm within a particular vicinity of a boundary determined from the hill-climbing algorithm. An exemplary score of 5 means at least 5 points classified as a boundary are within a particular vicinity of a boundary determined by the hill-climbing algorithm. The particular vicinity used can be based upon, for example, empirical evidence, the typical width or size of a true boundary, or other factors.

In some cases, the best result would be achieved earlier than the 6th merging step and it is possible to get an over-merged result at step 6. In this case one could use the result at step 5 manually or attempt to separate manually just the teeth that are over-merged. Sometimes, an under-merged or over-segmented result can occur even after step 6. In this scenario, by using a cursor control device and user interface a user could manually select ("click on") and merge the segments that require merging to extract the teeth correctly, for example. The final segmented digital 3D model can then be stored in an electronic storage device for later processing.

Table 6 provides exemplary pseudocode for implementing the algorithm for merging hill-climbing segmentation with point classification (machine learning) segmentation. For the alternative intestice detection segmentation, Table 7 provides exemplary pseudocode for implementing the algorithm for merging hill-climbing segmentation with interstice detection segmentation.

TABLE 6

Pseudocode for Merging Hill-Climbing
and Machine Learning Prediction

Input: a 3D mesh with a set of vertices V specified in 3D coordinate system X, Y and Z. Y represents the vertical axis or the general direction in which the teeth point upwards. The mesh also has a set of triangulations or faces F based on the vertices. Label assignments from hill climbing and boundary vertex labels predicted by the machine learning are also provided.
Output: Segmented mesh, where for each vertex $v_i$ in the mesh, a label $l_i$ corresponding to the segment to which that vertex belongs is assigned.
Assumptions: Teeth are roughly pointing up along the Y axis. The mesh has been truncated below the gum line.
Method steps:
1    Convert hill-climbing label assignments to boundaries between segments and interior vertices of segments resulting in a set of boundaries B
2    Eliminate small boundary prediction regions in the machine learning prediction by way of morphological erosion. Also eliminate boundaries which are misaligned with the general orientation of the quadrant/arch
3    Initialize merge threshold to Th
4    For each boundary $b_i$ in B, compute the score of the boundary by determining the number of machine learning predicted boundary vertices in the immediate neighborhood of the boundary. Normalize this number by the length of the boundary (total number of vertices)
5    Eliminate the boundaries which have a score less than Th and merge the segments appropriately by eliminating some cluster assignments and copying cluster assignments.
6    Recompute the boundary scores according to step 4
7    Increase Th by a predetermined
8    Repeat steps 5 to 7, 5 more times
9    Assign new cluster labels to vertices

TABLE 7

Pseudocode for Merging Hill-Climbing
Segments using Interstice Detection

Input: a 3D mesh with a set of vertices V specified in 3D coordinate system X, Y and Z. Y represents the vertical axis or the general direction in which the teeth point upwards. The mesh also has a set of triangulations or faces F based on the vertices. Label assignments from hill climbing, as well as detected intersticial spaces, are also provided.
Output: Segmented mesh, where for each vertex $v_i$ in the mesh, a label $l_i$ corresponding to the segment to which that vertex belongs is assigned.
Assumptions: Teeth are roughly pointing up along the Y axis.
Method steps:
1    Each detected intersticial space defines a plane in the 3D space of the mesh. For each segment found in Hill-Climbing, compute which side of each interstice plane the majority of its vertices reside. This is referred to the "polarity" of each segment with respect to each intersticial plane.
2    Merge together segments that have the same polarities with respect to nearby intersticial planes.

As an alternative to point classification and interstice detection, the algorithm can merge the hill-climbing segmentation with user input identifying centroids of teeth (step 31 in method 22). This segmentation method requires input from a user at the beginning of the process. In particular, the user identifies the centroid of each tooth in the digital 3D model of teeth. For example, when viewing the digital 3D model of teeth, such as viewing the model in FIG. 2, on display device 16, the user can use input device 18, such as a cursor control device, to select ("click on") the centroid of each tooth in the model or otherwise identify the centroid. The centroid can include the actual centroid or an estimation of the centroid as perceived by the user. This user entered information is used as the initialization for the step of the segmentation which merges the hill-climbing segments using the Kmeans method. These user-identified centroids need to be close to actual centroids of the teeth in order for the segmentation process to work well and not require post-processing by the user. The only parameter required for this method to be trained is $\epsilon$ in SVR for normal direction extraction described above for the alignment process.

The user-entered information to identify the centroids of each tooth is then merged with the results of the hill-climbing segmentation using the Kmeans clustering method. The vertices should first be replaced by the corresponding local maximum from the hill-climbing step. Then Kmeans method is applied on the new set of vertices to cluster them in k segments, where k is equal to the number of inputs ("clicks") of the user at the beginning of the process. The user's inputs (estimation of teeth centroids) are used as the centroid starting locations of the Kmeans method.

This merging method can result in successful segmentation as follows: clustering is applied on the local maxima (mostly located on the teeth cusps) and not the full mesh, yielding accuracy and speed benefits. The local maxima of larger clusters find higher weights in Kmeans method, and the centroid starting locations entered by the user avoid converging to other possible local optima of Kmeans methods.

Table 8 provides exemplary pseudocode for implementing the algorithm for merging hill-climbing segmentation with user-entered estimations of teeth centroids.

TABLE 8

Pseudocode for Merging Hill-Climbing Segments using Kmeans

Input: a 3D mesh with a set of vertices V specified in 3D coordinate system X, Y and Z, the segmentation result from the hill-climbing segmentation algorithm, in which the local maximum coordination that has been reached by each vertex is reported, and the estimation of centroids of teeth, which has been received from the user at the beginning of the process.
Output: Segmented mesh, where to each vertex $v_i$ in the mesh, a label $l_i$ corresponding to the segment to which that vertex belongs is assigned.
Method steps:
1  Represent/substitute each vertex with the local maximum it has reached.
2  Apply the Kmeans clustering method on the new vertices, with the user's centroid estimation as the centroid starting locations of the Kmeans.
3  Assign all vertices to a segment assigned to the corresponding local maximum value in step 2
4  Assign the appropriate cluster labels to each vertex.

The exemplary pseudocode in Tables 1-8 is provided for illustrative purposes of particular implementations of the described algorithms, and other implementations are possible.

Tooth Wear Estimation and Prediction

In one approach, a single scan of a patient's dentition for a person presumed to have tooth wear is compared to an estimated reconstruction of the original "virgin" tooth shape for each tooth or particular teeth (i.e., the shape before any tooth wear occurred), as predicted by a mathematical model as applied to the current patient's teeth. This approach can be summarized according to the following steps: a 3D scan of the patient's teeth is acquired; the individual teeth are segmented from one another using a segmentation algorithm; for each tooth comprising the patient's dentition, the original "virgin" shape of the tooth is predicted using a mathematical model of tooth shape learned from a large database of teeth; and the current scan of each tooth is compared to the predicted virgin tooth shape in order to assess the degree of wear that has occurred.

Figure 10:
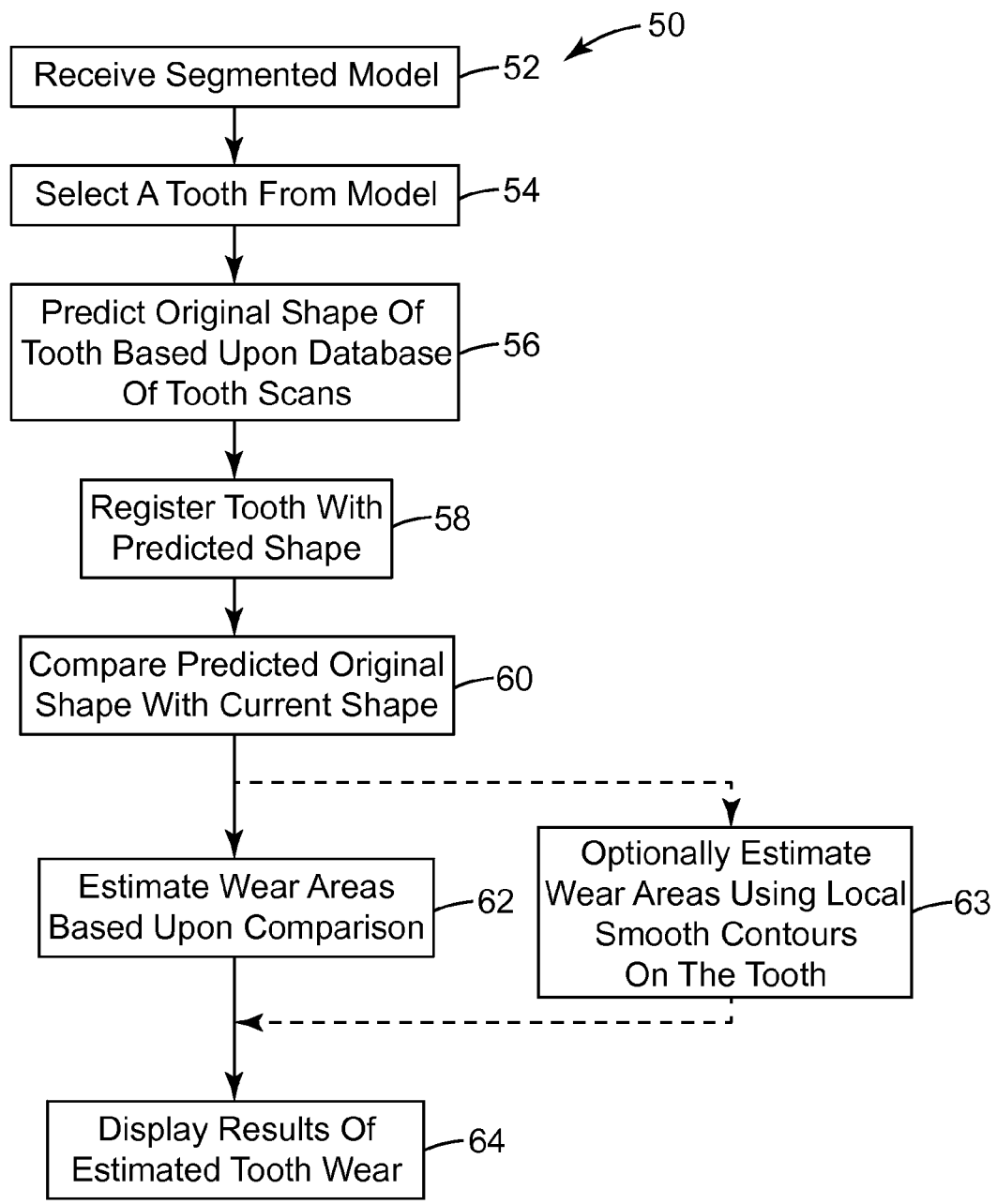
FIG. 10 is a flow chart of a method of estimating tooth wear using 3D scans.

FIG. 10 is a flow chart of a method 50 to implement this approach of estimating tooth wear using 3D scans. Method 50 can be implemented in software or firmware modules, for example, for execution by processor 20. Method 50 can alternatively be implemented in hardware modules or a combination of software and hardware. Method 50 includes receiving a segmented model (step 52), for example from the segmentation methodology described above.

A tooth is selected from the model (step 54), and the original "virgin" shape of the tooth is predicted based upon a database of tooth scans (step 56). In order to accomplish this, a large database of 3D tooth models can be accessed and used, where the degree of wear in each of the teeth in the database is known. Given this database, an aggregate generic mathematical model can be formed of the canonical original "virgin" shape of a tooth location. This can be accomplished for each tooth. For teeth that have a large variability in shape from person-to-person, multiple "virgin" models can be formed, which can include clustering of the space of tooth shape for that particular tooth location.

Given this database and the mathematical shape models learned from it, the original "virgin" shape of a tooth from the current scan can be predicted. Several approaches exist for performing this step. One approach is as follows. First, the appropriate model from the database for the current tooth is determined, since multiple clustered models may exist for each tooth location, depending on the variability of tooth shape at this bite location. If multiple models exist for this tooth, the appropriate model is determined by computing the similarity of this tooth to each model. Then, a mapping is computed from the current tooth to the model tooth shape. This mapping can be accomplished through use of a non-rigid registration algorithm. Then, once the new tooth is mapped to the model space, its original "virgin" shape is associated with that of the model. Using the inverse of the mapping estimated previously, this model is mapped back to the space of the current tooth, resulting in a prediction of the original shape of this tooth.

Once the original "virgin" tooth shape has been estimated, it can be compared with the actual current shape in order to assess the amount of wear exhibited (step 60). First, these two models may need to be registered (step 58), using a 3D registration algorithm, so that they are aligned with one another as closely as possible. An example of a registration algorithm is disclosed in the application referenced above. Then, the areas in which the actual and predicted "virgin" models are in disagreement must be located and compared (step 62). These represent the areas of the tooth that have been worn.

Wear areas can optionally be estimated using local smooth contours on the tooth (step 63), and this estimation can be used to supplement the estimated wear areas from step 62. In particular, local discontinuities in the tooth surface can be detected by analysis of the smooth contours in the digital model localized on or near the top surface of the tooth. A discontinuity in the model of that surface satisfying particular criteria can tend to indicate a worn area. The results of the estimated tooth wear, such as the heights or volumes of the worn areas, can be computed and displayed (step 64).

Figure 11:
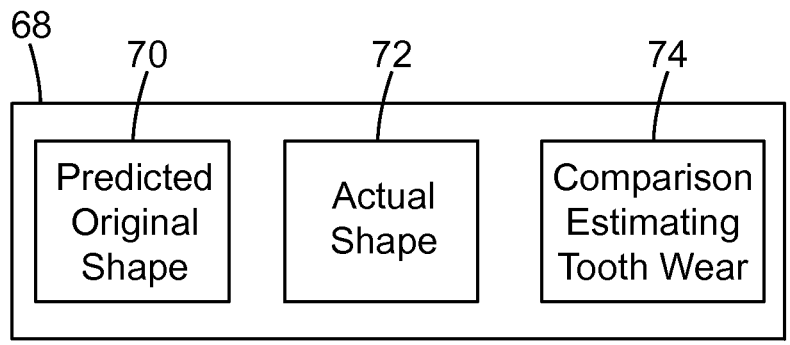
FIG. 11 is a diagram of a user interface for displaying estimated tooth wear.

FIG. 11 is a diagram of a user interface 68 for displaying estimated tooth wear, for example on display device 16. User interface 68 includes a section 70 for displaying a predicted original shape of the selected tooth, a section 72 for displaying the actual shape as shown in a 3D scan, and a section 74 for displaying a comparison of the shapes to indicate tooth wear. Section 74 can display, for example, the model of the actual shape superimposed on the model of the predicted original shape.

Another approach involves predicting tooth wear by determining from a single 3D scan of a person's dentition a score or a rating an amount of tooth wear for that person. This approach takes advantage of a large number of annotated 3D scan data of dentitions that have been given scores related to tooth wear. For example, the Smith and Knight tooth wear index could be used for annotating scans. Given these annotations this approach learns a mapping function that uses low-level mesh features such as curvature, spin images, and the features to predict the Smith and Knight tooth wear index for a particular tooth. Such an approach has a benefit for predicting the onset of conditions such as Bruxism at an early stage without the requirement of multiple scans spread out over a longer period of time.

Figure 12:
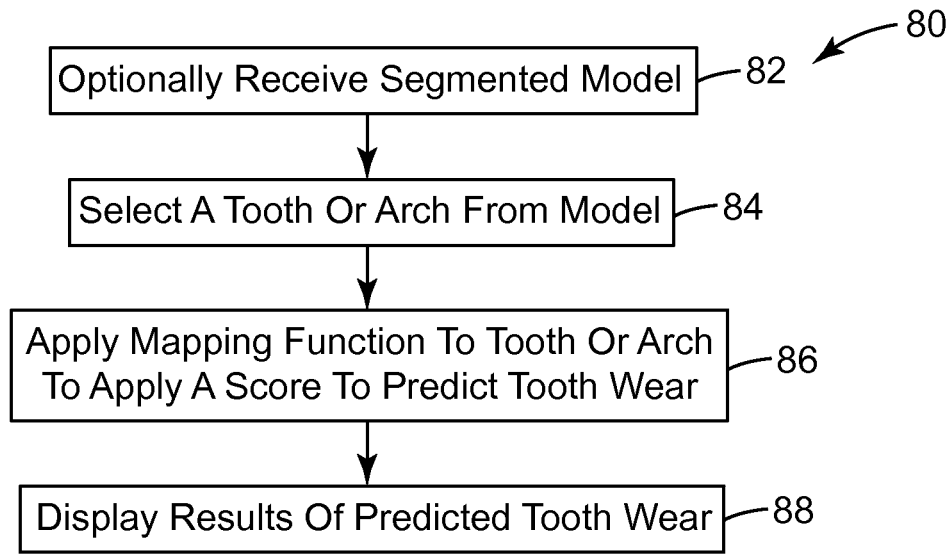
FIG. 12 is a flow chart of a method of predicting tooth wear using 3D scans.

FIG. 12 is a flow chart of a method 80 to implement this approach of predicting tooth wear using 3D scans. Method 80 can be implemented in software or firmware modules, for example, for execution by processor 20. Method 80 can alternatively be implemented in hardware modules or a combination of software and hardware. Method 80 includes optionally receiving a segmented model (step 82), for example from the segmentation methodology described above. Segmentation is optional in that mapping can be applied to the full mesh or a portion of it, representing a full or partial arch of teeth in the digital model of the teeth. A tooth or arch is selected from the model (step 84), and a mapping function is applied to the selected tooth or arch to predict tooth wear (step 86). The results of the predicted tooth wear can be displayed (step 88).

Step 86 can be implemented as follows. Many low level mesh features can be computed using well known computer vision and geometric methods. Some examples are features such as multi-scale surface curvature, singular values extracted from Principal Component Analysis of local shape, shape diameter, distances from medial surface points, average geodesic distances, shape contexts, and spin images. Given the ensemble feature set for a mesh X, a function f is defined as follows: f: $X \rightarrow \{0, 1, 2, 3\}$, that is the function f maps the set of features X to a Smith and Knight tooth wear index which takes one of 4 values. In terms of classification, this is a 4-class classification problem. Many different types of classifiers are possible to model this function f. This function can be one or a combination of many classification methods such as support vector machines, decision trees, conditional random fields, or other methods. Support vector machines are known to provide a high a degree of separation between classes with the use of kernels by comparing the features in the appropriate kernel space. Decision trees and ensemble versions of decision trees/stumps such as boosting, bootstrapping, and other versions can be used to combine multiple weak classifiers into strong classifiers with very high performance. Finally, conditional random fields provide great performance by taking neighborhood and group labeling into account. This can be used for localized classification such as classifying the top portion of teeth, i.e. the cusps. Bag-of-features are also possible for use in classifying objects globally by the weighted assimilation of local mesh features computed all over the mesh.

Figure 13:
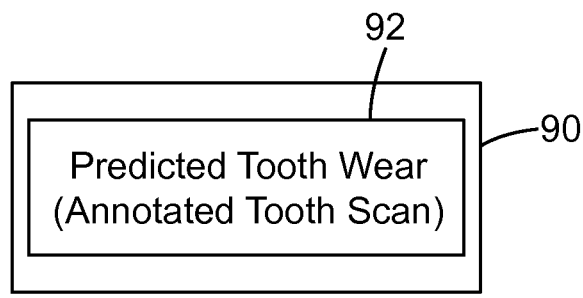
FIG. 13 is a diagram of a user interface for displaying predicted tooth wear.

FIG. 13 is a diagram of a user interface 90 displaying predicted tooth wear, for example on display device 16. User interface 90 includes a section 92 for displaying predicted tooth wear by showing, for example, an annotated scan of the selected tooth.

The invention claimed is:

1. A method for estimating teeth wear, comprising steps of:
   receiving a 3D digital model of teeth;
   segmenting the 3D digital model of teeth to identify individual tooth within the 3D digital model of teeth and generate a segmented 3D digital model of teeth;
   selecting a digital model of a tooth from the segmented 3D digital model of teeth;
   predicting an original shape of the selected tooth to obtain a digital model of a predicted original shape; and
   comparing the digital model of the tooth with the digital model of the predicted original shape to estimate wear areas in the selected tooth.

2. The method of claim 1, wherein the segmenting step comprises:
   performing a first segmentation method that over segments at least some of the teeth within the 3D digital model of teeth and outputs as results the 3D digital model of teeth with the over segmentation;
   performing a second segmentation method that classifies some points within the 3D digital model of teeth as being on an interior of a tooth in the 3D digital model of teeth and classifies some other points within the 3D digital model of teeth as being on a boundary between teeth in the 3D digital model of teeth and outputs as results the 3D digital model of teeth with the classification; and
   combining the results of the first and second segmentation methods to generate the segmented 3D digital model of teeth.

3. The method of claim 1, wherein the predicting step comprises selecting a digital model of a tooth from known tooth shapes based upon characteristics of a patient corresponding with the 3D digital model of teeth.

4. The method of claim 1, further comprising estimating wear areas in the selected tooth by detecting discontinuities in the digital model of the tooth that satisfy particular criteria.

5. The method of claim 1, wherein the comparing step comprises detecting differences in surface area between the digital model of the tooth and the digital model of the predicted original shape.

6. The method of claim 1, further comprising displaying an indication of the estimated wear areas.

7. A system for estimating teeth wear, comprising:
   a module for receiving a 3D digital model of teeth;
   a module for segmenting the 3D digital model of teeth to identify individual tooth within the 3D digital model of teeth and generate a segmented 3D digital model of teeth;
   a module for selecting a digital model of a tooth from the segmented 3D digital model of teeth;
   a module for predicting an original shape of the selected tooth to obtain a digital model of a predicted original shape; and
   a module for comparing the digital model of the tooth with the digital model of the predicted original shape to estimate wear areas in the tooth.

8. The system of claim 7, wherein the module for segmenting comprises:
   a module for performing a first segmentation method that over segments at least some of the teeth within the 3D digital model of teeth and outputs as results the 3D digital model of teeth with the over segmentation;
   a module for performing a second segmentation method that classifies some points within the 3D digital model of teeth as being on an interior of a tooth in the 3D digital model of teeth and classifies some other points within the 3D digital model of teeth as being on a boundary between teeth in the 3D digital model of teeth and outputs as results the 3D digital model of teeth with the classification; and a module for combining the results of the first and second segmentation methods to generate the segmented 3D digital model of teeth.

9. The system of claim 7, wherein the module for predicting comprises a module for selecting a digital model of a tooth from known tooth shapes based upon characteristics of a patient corresponding with the 3D digital model of teeth.

10. The system of claim 7, further comprising a module for estimating wear areas in the selected tooth by detecting discontinuities in the digital model of the tooth that satisfy particular criteria.

11. The system of claim 7, wherein the module for comparing comprises a module for detecting differences in surface area between the digital model of the tooth and the digital model of the predicted original shape.

12. The system of claim 7, further comprising a module for displaying an indication of the estimated wear areas.

13. The method of claim 6, wherein the display step comprises displaying the digital model of the tooth superimposed on the digital model of the predicted original shape.

14. The system of claim 12, wherein the module for displaying comprises a user interface displaying the digital model of the tooth superimposed on the digital model of the predicted original shape.

15. The method of claim 1, further comprising registering the digital model of the tooth with the digital model of the predicted original shape.

16. The system of claim 7, further comprising a module for registering the digital model of the tooth with the digital model of the predicted original shape.

* * * * *